(12) United States Patent  
Ginsberg

(10) Patent No.: US 7,608,038 B2  
(45) Date of Patent: Oct. 27, 2009

(54) LUMINAL COUPLING SYSTEM

(75) Inventor: Gregory G. Ginsberg, Devon, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 909 days.

(21) Appl. No.: 10/513,315

(22) PCT Filed: May 16, 2003

(86) PCT No.: PCT/US03/15524

§ 371 (c)(1),  
(2), (4) Date: Nov. 3, 2004

(87) PCT Pub. No.: WO03/097124

PCT Pub. Date: Nov. 27, 2003

(65) Prior Publication Data

US 2005/0177174 A1 Aug. 11, 2005

Related U.S. Application Data

(60) Provisional application No. 60/381,201, filed on May 17, 2002.

(51) Int. Cl.  
*A61B 1/00* (2006.01)  
*A61M 3/00* (2006.01)  
*A61F 11/00* (2006.01)
(52) U.S. Cl. .......................... 600/104; 604/44; 606/108
(58) Field of Classification Search .................. 600/12, 600/104; 604/43–44, 115–116, 164.01, 175; 606/108  
See application file for complete search history.

(56) References Cited

U.S. PATENT DOCUMENTS

| | | | |
|---|---|---|---|
| 3,043,309 A | * | 7/1962 | McCarthy .................... 604/540 |
| 3,961,632 A | | 6/1976 | Moossun |
| 4,077,412 A | * | 3/1978 | Moossun ............... 604/103.03 |
| 4,671,287 A | * | 6/1987 | Fiddian-Green ............ 600/363 |
| 4,758,219 A | * | 7/1988 | Sacks et al. .................. 604/506 |
| 4,798,592 A | * | 1/1989 | Parks ........................ 604/500 |

(Continued)

OTHER PUBLICATIONS

Ginsberg, Gregory G., MD, "Direct Percutaneous Endoscopic Jejunostomy", University of Pennsylvania Health Systems, pp. 205-209, 2001.  
Ginsberg, Gregory G., MD, "Techniques in Gastrointestinal Endoscopy", University of Pennsylvania Health Systems, vol. 3, No. 1, pp. 42-49, 2001.

*Primary Examiner*—John P Leubecker  
*Assistant Examiner*—Philip R Smith  
(74) *Attorney, Agent, or Firm*—RatnerPrestia

(57) ABSTRACT

A luminal coupling tube system for providing access to a lumen of a subject is disclosed. The system includes an internal magnet assembly, a snare assembly, an external magnet, a pull wire system and a feeding tube assembly. The internal magnet assembly includes an internal magnet having a first coupling surface and a tether for traversing an endoscope instrument channel. The snare assembly includes a snare, a snare operating device, and a cable. The external magnet includes a second coupling surface. The polar orientation of the external magnet is opposite the polar orientation of the internal magnet such that the first and second coupling surfaces are magnetically attracted. The pull wire system includes a needle, a cannula and a pull wire. The feeding tube assembly includes a tube, a snare, a connector, and a dome fixed to the tube. A method of use is disclosed.

16 Claims, 6 Drawing Sheets

U.S. PATENT DOCUMENTS 4,809,713 A * 3/1989 Grayzel ...................... 607/116
5,431,640 A * 7/1995 Gabriel ...................... 604/270
5,681,260 A * 10/1997 Ueda et al. .................. 600/114
7,169,104 B2 * 1/2007 Ueda et al. .................. 600/104

* cited by examiner

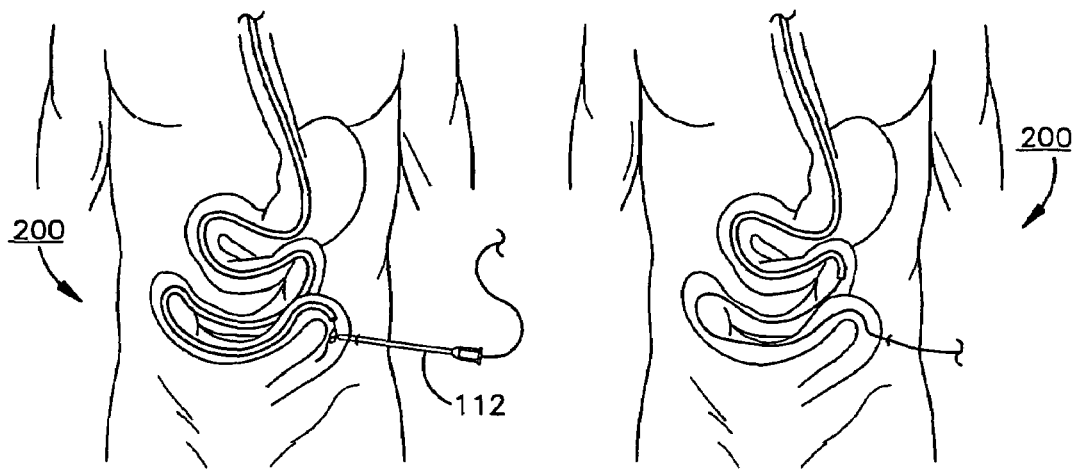
Fig.1E
(PRIOR ART)
Fig.1F
(PRIOR ART)
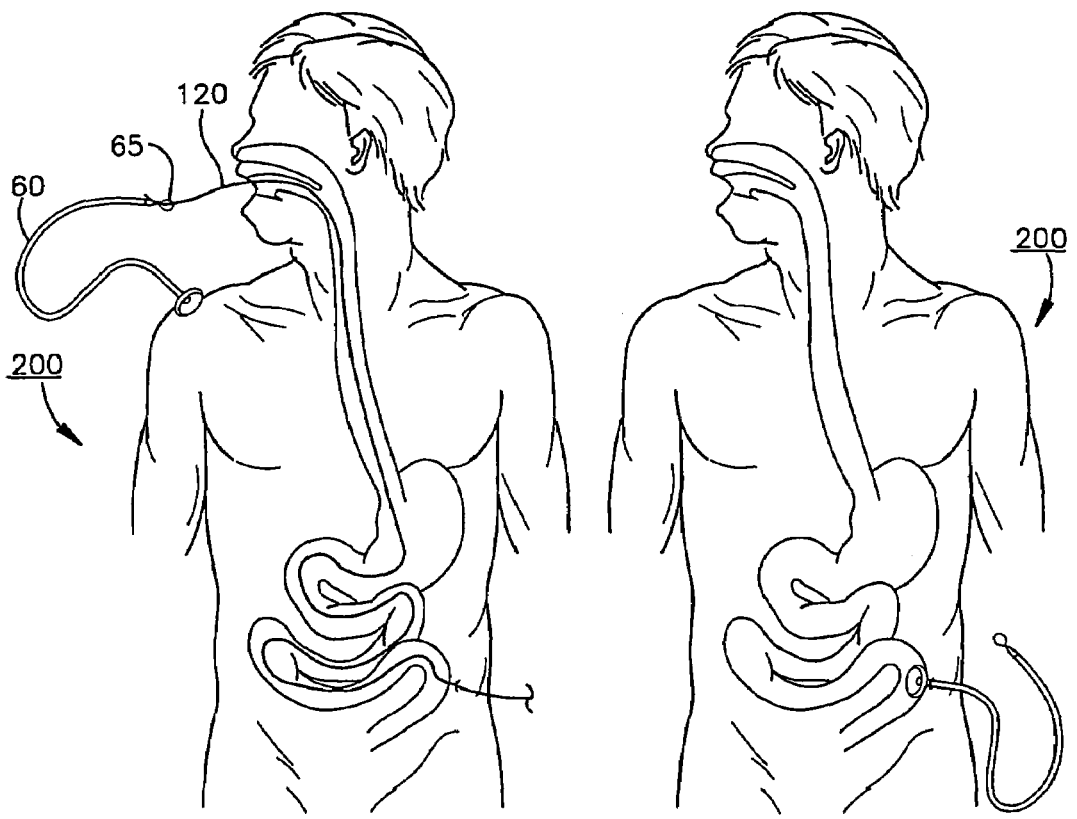
Fig.1G
(PRIOR ART)
Fig.1H
(PRIOR ART)

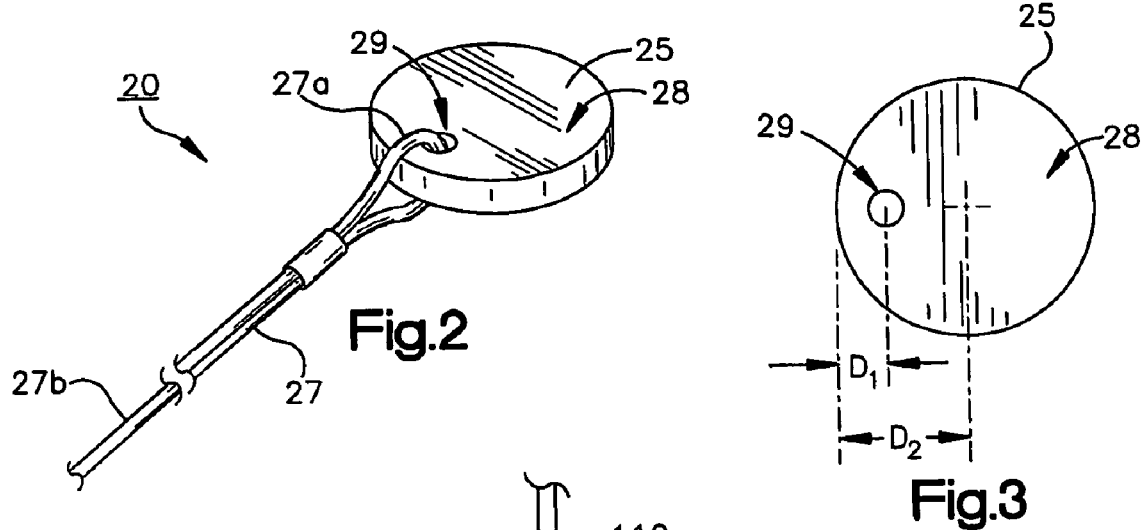
Fig.2
Fig.3
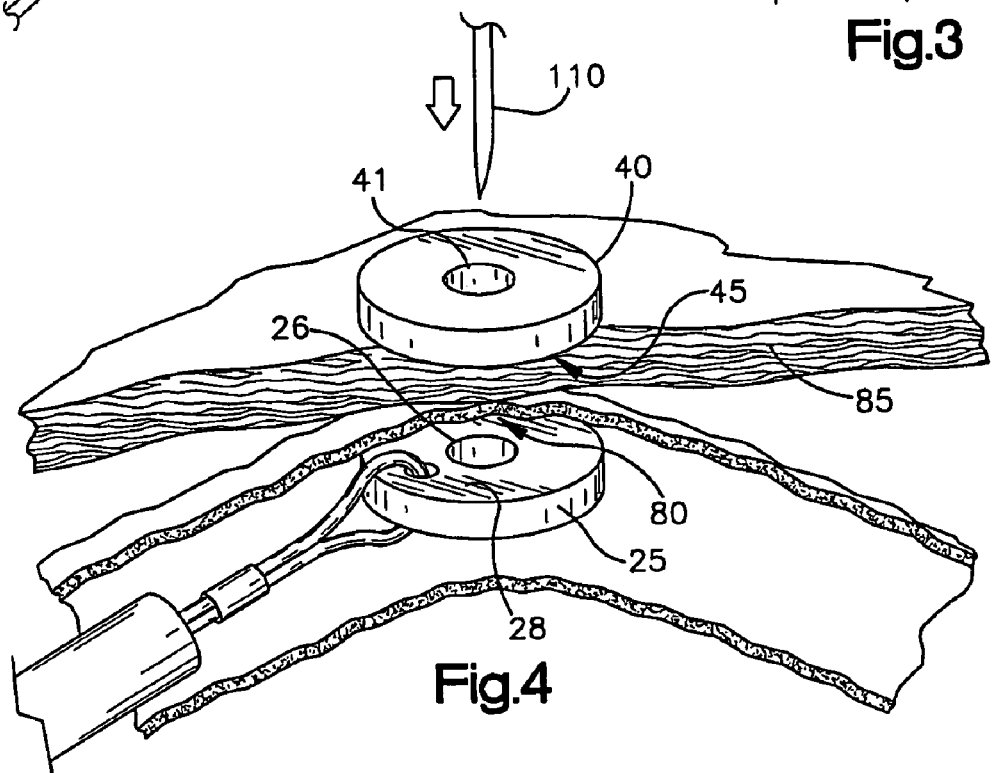
Fig.4
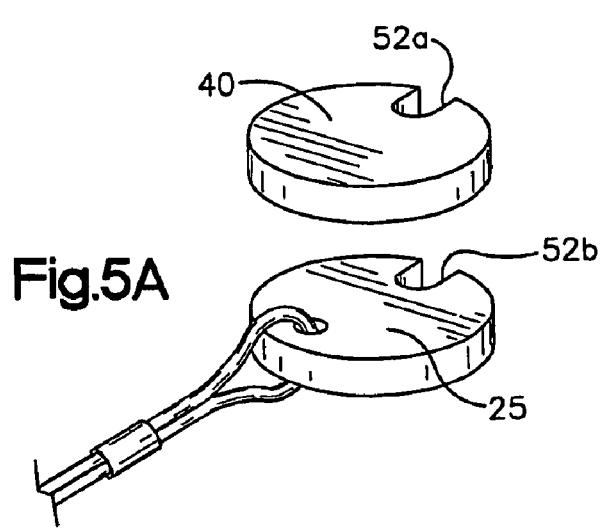
Fig.5A

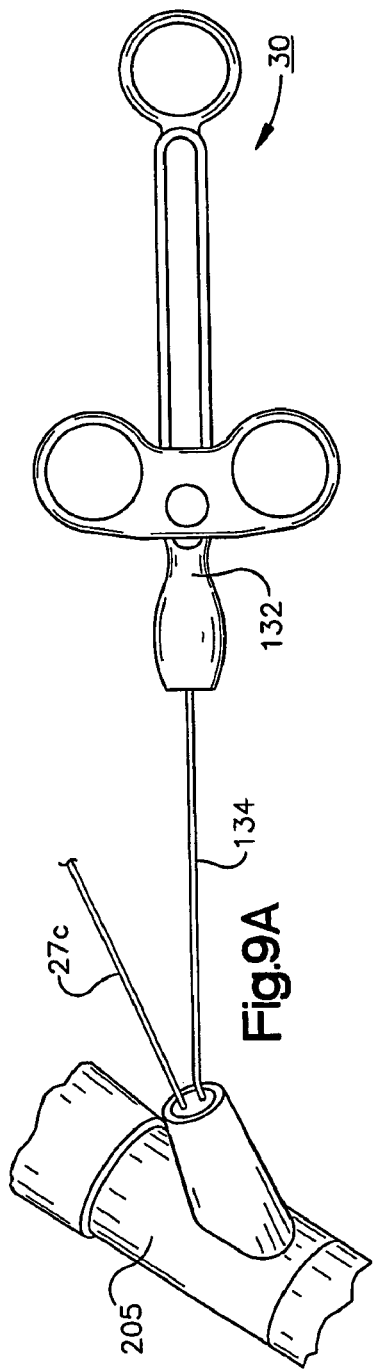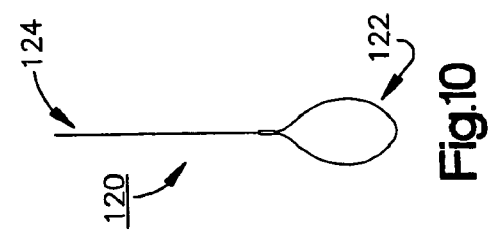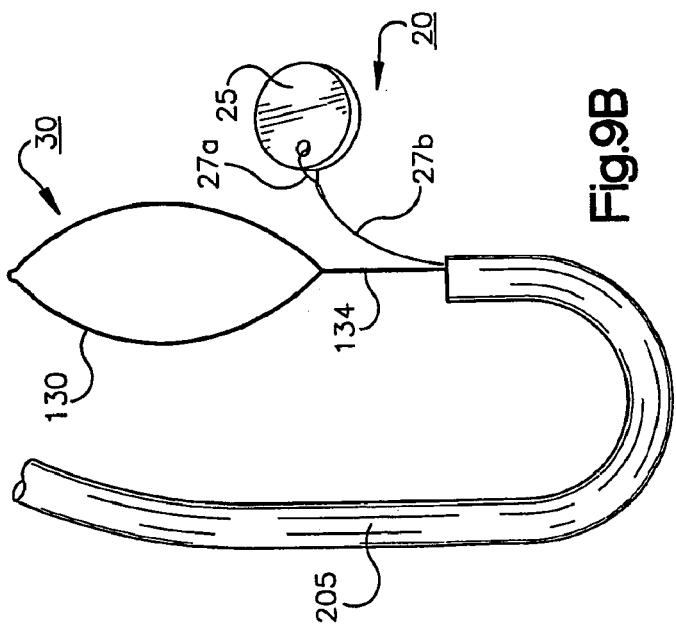

LUMINAL COUPLING SYSTEM

CROSS-REFERENCE TO RELATED APPLICATIONS

This PCT patent application claims benefit of U.S. Provisional Patent Application Ser. No. 60/381,201 entitled "Luminal Coupling System" and filed with the United States Patent and Trademark Office on May 17, 2002.

FIELD OF THE INVENTION

The present invention relates to a luminal coupling system and more particularly to a luminal magnetic coupling system for providing access directly to a lumen within a subject.

BACKGROUND OF THE INVENTION

Many different medical protocols require a surgeon to access a lumen, or organ, with a body. One frequent occurring protocol is the need to supply nutritional directly to the gastrointestinal tract.

Various techniques for providing nutritional to a subject are in widespread use in hospitals, nursing homes, and other medical facilities. Most techniques include either feeding the subject intravenously or directly into the gastrointestinal tract through the mouth. Protocol for certain medical conditions calls for feeding directly into the gastrointestinal tract, rather than into a vein. Most of these conditions involve inserting a tube through the nose or mouth into the esophagus. However, certain known techniques are not available in specific cases due to a surgically altered anatomy, a gastric outlet obstruction, or an increased risk of gastro-respiratory reflux. These and certain other conditions require direct jejunal feeding.

Conventional jejunal feeding methods include a naso-jejunal tube, a surgical jejunostomy, interventional radiologic jejunostomy and direct percutaneous endoscopic jejunal system. The naso-jejunal tube is uncomfortable, visually not appealing, and has a tendency to clog. The surgical jejunostomy and interventional radiologic jejunostomy can be effective procedures, but are prohibitively expensive. The direct percutaneous endoscopic jejunal procedure is technically challenging and beyond the comfortable skill range of many surgeons. Specifically, the lumen, or cavity of the tubular-shaped bowels, is not fixed during the procedure, making properly inserted without injury or undesirable effects difficult.

The present invention provides a new and improved luminal magnetic coupling system for providing access directly to a lumen within a subject. The present invention uses magnetically coupling internal and external magnets to provide an inexpensive, precise and technically achievable system and method.

SUMMARY OF THE INVENTION

In an illustrated embodiment of the invention a luminal magnetic coupling system for providing access directly to a lumen within a subject is provided. The luminal magnetic coupling system includes an internal magnet assembly, a snare assembly, an external magnet, a pull wire system and a feeding tube assembly.

The internal magnet assembly is inserted into an endoscope instrument channel. The internal magnet assembly includes an internal magnet and a tether. The internal magnet includes a first coupling surface defining a surface shape and size. The internal magnet is characterized by a polar orientation and a magnetic strength. The tether includes a first end portion fixed to the magnet, a second end portion disposed remote from the first end portion, and a middle portion spaced between the first and second end portions. The middle portion traversing the endoscope instrument channel.

The snare assembly includes a snare, a snare operating device, and a cable connecting the snare to the snare operating device.

The external magnet includes a second coupling surface defining a surface shape and size. The external magnet is characterized by a polar orientation and a magnetic strength. The polar orientation of the external magnet is opposite the polar orientation of the internal magnet such that the first and second coupling surfaces are magnetically attracted to each other.

The pull wire system includes a needle, a cannula and a pull wire. The pull wire comprises a mating end and a pull end.

The feeding tube assembly includes a tube having a first end and a second end, a snare, a connector fixedly joining the tube first end to the snare, and a dome fixed to the tube second end.

The dome may include a bottom surface having a tube mounting hole and an annular-shaped perforated side surface. The perforated side surface is designed to distribute liquid in a plurality of radial directions.

The magnetic strength of the internal magnet and the magnetic strength of the external magnet may be collectively sufficient to magnetically couple the internal and external magnets when juxtaposed of either side of an lumen wall.

The magnetic strength of the internal magnet and the magnetic strength of the external magnet may be of collectively sufficient strength to stabilize an intestinal lumen to an abdominal wall when the magnets are juxtaposed of either side of an abdominal wall.

The surface shape and size of the first coupling surface and the surface shape and size of the second coupling surface may be essentially the same.

The external magnet may comprise structure defining a needle insertion zone. The internal magnet may comprise structure defining a needle acceptance zone. The needle insertion zone and the needle acceptance zone may cooperatively align when the external magnet and the internal magnet are magnetically coupled.

The present invention offers advantages over devices available in the prior art. The system is inexpensive and easy to use. Patient recover time and risk of infection is reduced over certain prior art systems and methods.

Further features and advantages of the invention will become apparent from the following detailed description made with reference to the accompanying drawings.

BRIEF DESCRIPTION OF THE DRAWINGS

FIGS. 1A-1H are a series of schematic views of a prior art system used to insert a feeding tube directly into the small intestine of a subject;

FIG. 2 is a perspective view of a part of a system constructed in accordance with a preferred embodiment of the present invention, showing an internal magnet assembly;

FIG. 3 is a top view of the internal magnet illustrated in FIG. 2;

FIG. 4 is a perspective view of several parts of a system of the present invention, showing the internal magnet assembly magnetically coupled to, and cooperatively aligned with, an external magnet to advantageously allow needle insertion through each magnet;

FIG. 5a is a perspective view of an alternative design of the parts illustrated in FIG. 4, showing an alternative design of a needle insertion zone and a needle acceptance zone;

FIG. 5b is a perspective view of an alternative design of the parts illustrated in FIG. 4, showing the design of a needle insertion zone and a needle acceptance zone illustrated in FIG. 5a;

FIG. 9a is a perspective view of a part of a system of the present invention installed in an endoscope instrument channel, showing a snare assembly and an internal magnet assembly at the proximal end of the endoscope with respect to the user;

FIG. 9b is a perspective view of a part of a system of the present invention installed in an endoscope instrument channel, showing a snare assembly and an internal magnet assembly at the distal end of the endoscope with respect to the user;

FIG. 10 is a perspective view of a part of a system of the present invention, showing a pull wire;

BEST MODE CONTEMPLATED FOR CARRYING OUT THE INVENTION

A luminal magnetic coupling system for providing access directly to a lumen is disclosed. The system may be used for any medical procedure that requires access to a lumen within a subject. For exemplary purposes only, the system will be described for use in an endoscopic feeding tube installation into the small intestines. In this example, the system is constructed and arranged so that a surgeon can easily and confidently perform a direct percutaneous endoscopic jejunal feeding tube installation.

The system is designed for use with any suitable or conventional endoscopic surgical equipment. For purposes of this description, the system is described in the context of use with an optical endoscopic apparatus. A suitable endoscope will have an elongated body and an instrument channel. Surgical instruments, such as portions of the system constructed in accordance with the present invention, may be introduced through an instrument channel, which extends axially throughout the body of the scope. In addition, the scope may have optical and illumination features that are used by the surgeon during the practice of this invention.

Figure 1A:
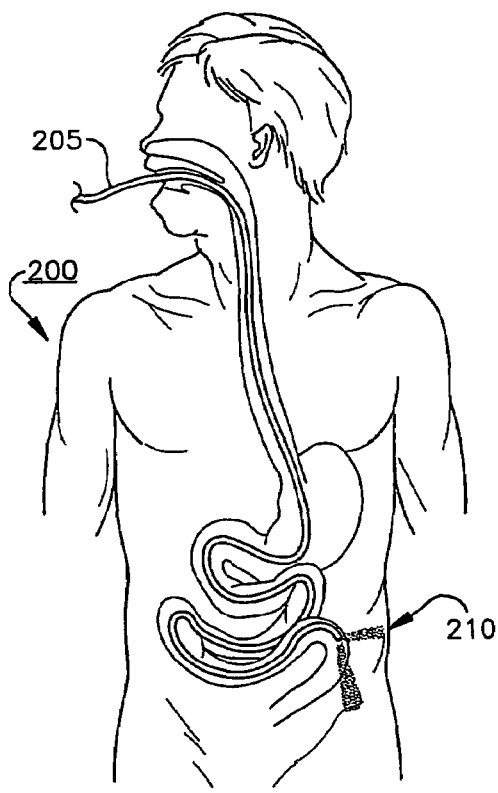
Figure 1B:
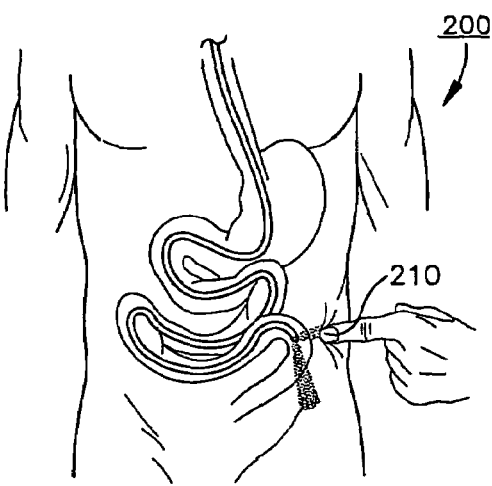
Figure 1C:
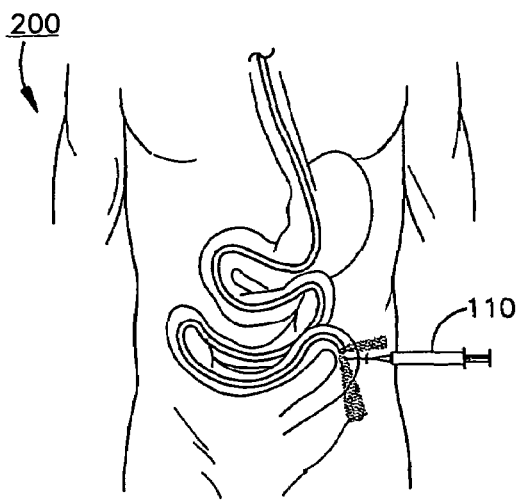

The system contains several specific advantages over known prior art techniques, including the technique illustrated in FIGS. 1a-1h. As seen in FIG. 1a, the prior art technique relies upon the imprecise transillumination of the endoscope 205 to determine a needle insertion point 210 in a subject 200. The present invention uses a magnet system to determine a desired location within the intestine for installing a feeding tube. Further, the present invention uses magnets featuring a needle insertion zone and a needle acceptance zone for determining a precise insertion point for a sounding needle.

Referring now to the FIGS. 2-6, 9b and 10, the system includes an internal magnet assembly 20, a snare assembly 30, an external magnet 40, a pull wire system 120 and a feeding tube assembly 60.

Referring first to FIG. 2, the internal magnet assembly 20 includes an internal magnet 25 and a tether 27. The internal magnet includes a first coupling surface 28 defining a surface shape and size. The internal magnet 25 is characterized by a polar orientation and a magnetic strength. The tether 27 includes a first end portion 27a fixed to the magnet 25 and a second end portion 27c (not shown) disposed remote from the first end portion, and a middle portion 27b spaced between the first and second end portions. The middle portion 27b traversing the endoscope instrument channel when installed.

The magnet 25 may be fixed to the tether in any conventional manner. As illustrated in FIG. 2, the tether end portion 27a is inserted through a mounting hole 29 in the magnet. FIG. 3 shows a possible location of a mounting hole when viewing the magnet from the top. As shown, the mounting hole is located a distance $D_1$ from the center point of the magnet. In one embodiment, the distance $D_1$ is less then half of the distance $D_2$, the radius of the magnet. The mounting hole may be formed by a laser drilling technique.

Any suitable magnet may be used in the practice of this invention. A preferred magnet is constructed from one or more rare earth metals. One preferred magnet is constructed of Neodymium Iron Boron (NdFeB). In an alternative design of the present invention, only one of either the internal disk or external disk are actually magnetic, while the other disk is merely iron.

Any suitable magnet size providing a sufficient field of concentration may be used in the practice of this invention. However, it is believed the ability to successfully perform the present invention is increased with decreasing magnet size. An internal magnet of the preferred embodiment has a width not greater than 1 inch. The preferred magnet is about 0.75 inches in diameter. Although not wanting to be bound by theory, it is believe a magnet of this reduced size provides a magnetic field of increased concentration over a smaller surface area. This advantageously permits internal and external magnet alignment, and decreases the risk of improper needle insertion. A magnet for the practice of this invention is commercially available from Edmund Industrial Optics, at fax number (856) 573-6295. This exemplary magnet has a strength of 11.0 lbs. lift.

Referring now to FIG. 4, a perspective view of several parts of a system of the present invention is shown. Specifically, an internal magnet 25 is shown magnetically coupled to, and cooperatively aligned with, an external magnet 40. The structure of the internal magnet 25 and the internal magnet 40 advantageously allow a needle 110 to be inserted through the magnets 25, 40. Specifically, the needle is inserted through a needle insertion zone define by a void 41 in the external magnet 40 and an needle acceptance zone define by a void 26 in the internal magnet 26.

In the preferred embodiment, the internal magnet is coated with a biocompatible material. This coating advantageously prevents the magnet from reacting with the corrosive environment of the gastrointestinal tract, preventing undesired reaction by-products from entering the subject. The coating may be silicon or any other suitable coating known to one with ordinary skill in the art.

As illustrated, the lumen 80, i.e., duct wall of a tubular organ, is stabilized against a portion of the abdominal wall 85 disposed at the internal target location. The improvement of the stabilizing of the lumen 80 advantageously permits ease of certain method steps of the present invention.

As illustrated, external magnet 40 includes a second coupling surface 45 defining a surface shape and size. The external magnet is characterized by a polar orientation and a magnetic strength. The polar orientation of the external magnet is opposite the polar orientation of the internal magnet such that the first and second coupling surfaces 28, 45 are magnetically attracted to each other.

Figure 5B:
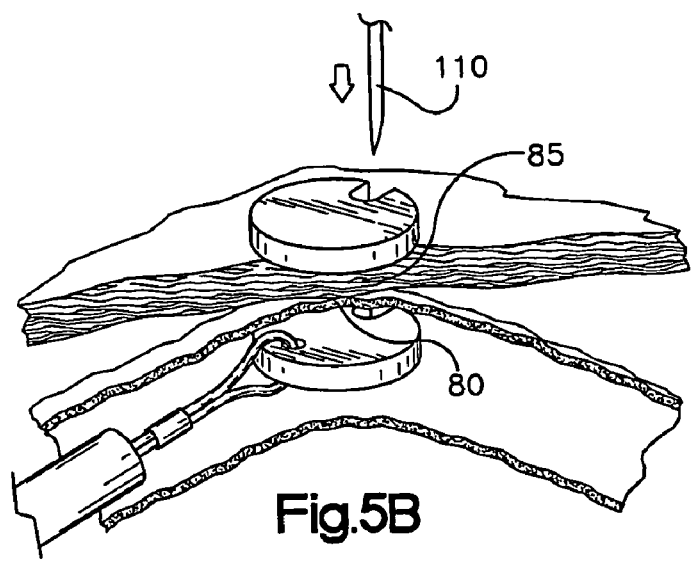

Referring to FIG. 5a, a perspective view of an alternative design of the parts illustrated in FIG. 4 is shown. The alternative design features a different needle insertion zone 52a and needle acceptance zone 52b. FIG. 5b is a perspective view of a design featuring the needle insertion zone and a needle acceptance zone illustrated in FIG. 5a.

Figure 11A:
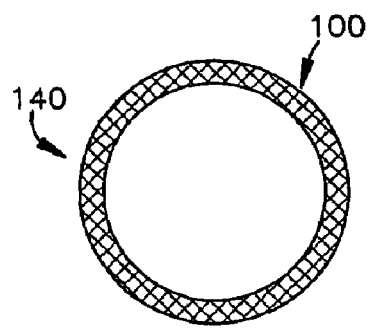
FIGS. 11a-11d are top views of alternative designs of a part of a system of the present invention, showing external magnets having varying needle insertion zones.
Figure 11B:
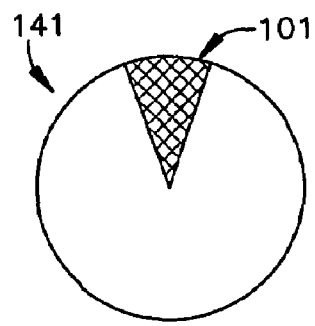
Figure 11C:
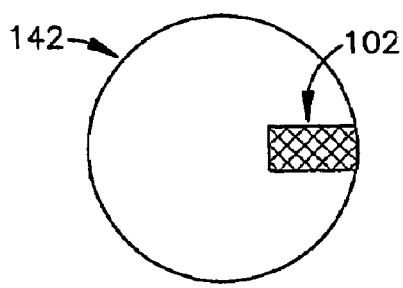
Figure 11D:
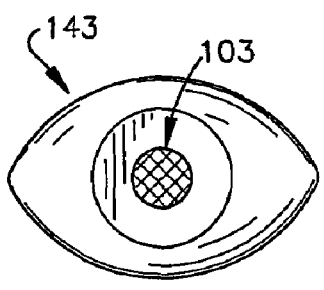

As illustrated in FIGS. 5A and 5B, the first coupling surface 28 and second coupling surface 45 have essentially the same shape and size. This allows for advantageous magnet aligning and precise needle insertion. As illustrated in FIGS. 11a-11d, external magnets 140, 141, 142, 143 of various structure are shown in top views. FIG. 11d as illustrated is an oblong-shaped ellipsoid having a top planar second coupling surface 28. Various needle insertion zones 100, 101, 102, 103 are illustrated in the top views provided. Any suitable needle insertion point within the zone may be chosen. Further, each magnet design may be used with one or more needle insertion zone design.

Figure 1D:
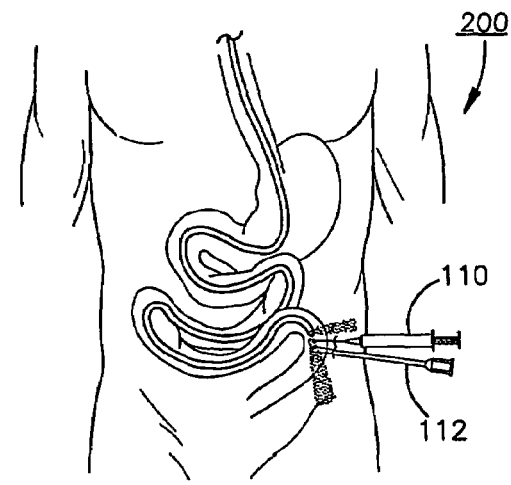
Figure 12:
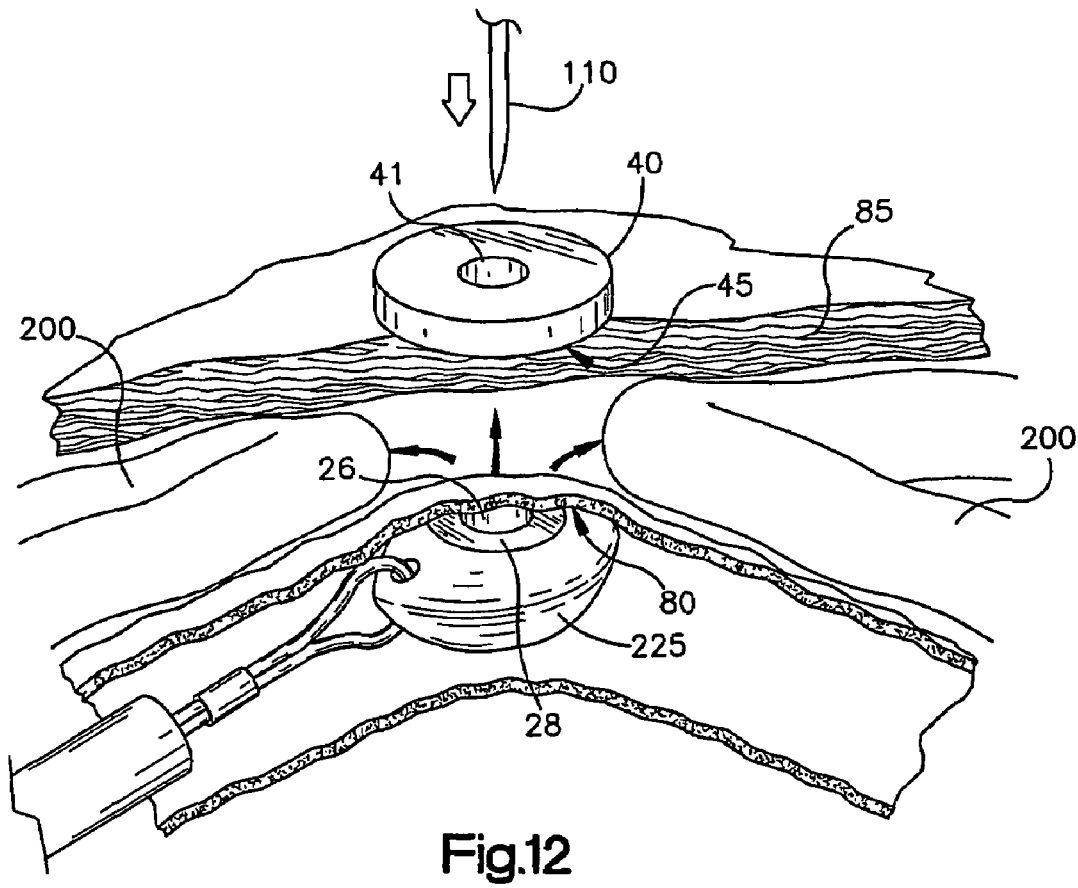
FIG. 12 is a perspective view of several parts of a system of the present invention, showing the internal magnet of FIG. 1d.

Although not wanted to be bound by theory, it is believe that the magnet shape shown in FIG. 11d will offer the least resistance as it is transported down the lumen tract, as well as having beneficial safety features. Referring now to FIG. 12, a perspective view of the internal magnet of FIG. 1d is shown in use within a subject. The internal magnet 225 is an oblong-shaped ellipsoid. This beneficial structure achieves a tunneling effect when transported within a lumen of a subject such that other tissue and organs are pushed distally away from the magnet. This negates a concern that any non-targeted organs could get positioned on or above the internal magnet and get carried up the other anterior abdominal wall 80 where they could be pierced with the introducer needle 110. FIG. 12 illustrates an internal magnet 225 that has pushed an internal intestine 200 away from the magnet such that no non-targeted tissue or organs are in the insertion path of the needle 110.

Figure 6:
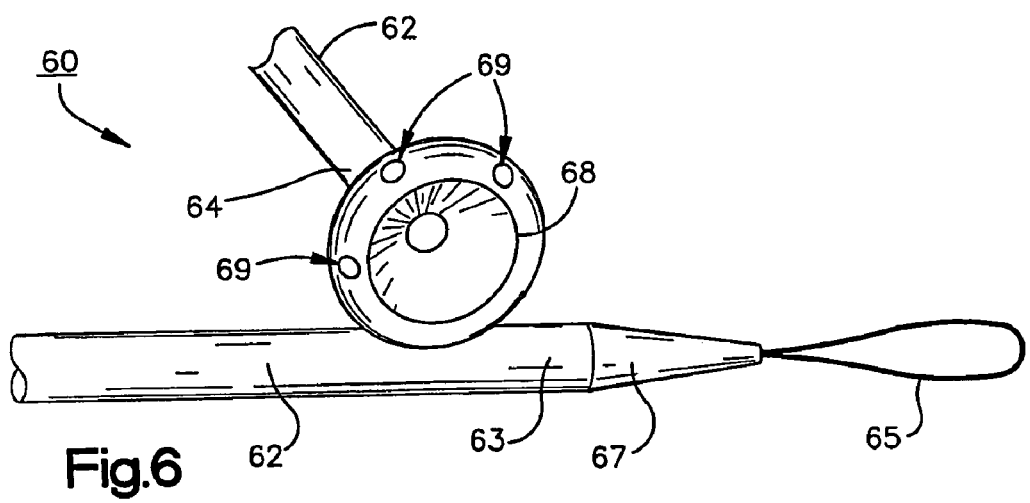
FIG. 6 is a perspective view of a part of a system of the present invention, showing a feed tube assembly.

An exemplary feeding tube assembly 60 is illustrated in FIG. 6. The feeding tube assembly 60 includes a tube 62 having a first end 63 and a second end 64, a snare 65, a connector 67 fixedly joining the first end 63 to the snare 65, and a dome 68 fixed to the tube second end 64. As shown, the connector 67 is advantageously cone-shaped to permit low-resistance travel through the lumen during installation of the feeding tube. The snare 65 may be used to attach to the mating end 122 of the pull wire 120 illustrated in FIG. 10.

The dome 68 includes a bottom surface having a tube mounting hole and an annular-shaped side surface including perforations 69. Once properly installed within a subject, the perforation advantageously distribute liquid in a plurality of radial directions.

Figure 7:
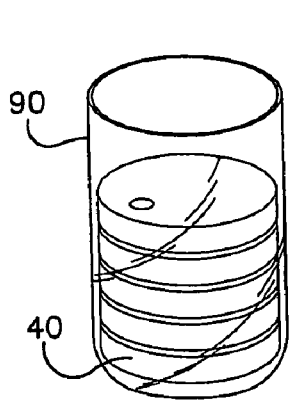
FIG. 7 is a perspective view of a part of a system of the present invention, showing a external magnet and a sleeve.

Referring again to the external magnet 40, in order to increase magnet strength without increasing the surface area of the second coupling surface, a stack of external magnets may be used as illustrated in FIG. 7. In FIG. 7, a stack of magnets is illustrated within a protective disposable sleeve 90. In the practice of the invention, the stack may be an assembly of magnets, with the assembly having a fixed stack height. Alternatively, the stack may include removably joined magnets of equal diameter. Depending on several factors, e.g., the obesity of the subject, the stack may be increased or decreased in height, and consequently, magnetic strength. Use of the sleeve 90 prevents bodily fluids from contacting one or more external magnets, allowing the stack to be reused.

A perspective view of a part of a system of the present invention installed in an endoscope instrument channel in shown in FIGS. 9a-9b. A snare assembly 30 and an internal magnet assembly 20 are shown at the proximal end of the endoscope with respect to the user. The snare cable 134 and the tether second end portion 27c are shown. A companion perspective view of the distal end of the system is shown FIG. 9b. Specifically, the snare 130 and the internal magnet 25 and the tether middle portion 27b and first end portion 27a are shown.

Method of Use

A method of the present invention will now be discussed. Dependent upon the medical condition of the subject, the surgeon must first determine into which portion of the gastrointestinal tract he or she wishes to install the feeding tube. For exemplary purposes, a discussion of the method of the present invention will focus on installing the tube into the jejunal region of the small intestines. It should be understood by others with ordinary skill in the art that the present invention could be utilized in other locations within the gastrointestinal tract.

The method may begin with the subject under conscious sedation. The internal magnet assembly is inserted into the instrument channel of the endoscope. This can be done by several methods, including entering the tether into the distal end of the device until the internal magnet is disposed proximal to the distal end of the scope. In this position, the second end portion of the tether is disposed remote from the proximal end of the endoscope.

Figure 8:
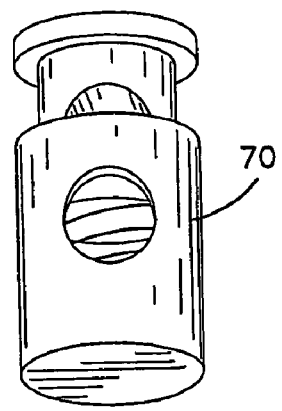
FIG. 8 is a perspective view of a part of a system of the present invention, showing a lock.

In the preferred embodiment, a lock is installed on the second end portion of the tether. The lock prohibits the internal magnet from moving relative to a distal end of an endoscope. Although the internal magnet can be rotated with respect to the scope, or moved slightly closer to the endoscope, it cannot move a greater distance away from the endoscope. By prohibiting the internal magnet from moving, the surgeon is afforded increased control. The lock may be any known lock type, including a bull dog clamp or a cord lock. A suitable cord lock, model number L105-6MM, is commercially available from A+ Products, Inc, at telephone number (718) 272-8544. A lock 70 is illustrated in FIG. 8.

After the internal magnet assembly 20 is installed, the snare assembly 30 may be installed in the same, or a parallel, instrument channel. Alternatively, the snare assembly 30 is installed later in the method. Loading the snare assembly after intubation is actually preferred because additional instruments in the instrument channel can cause stiffness in the scope and reduce flexibility of the elongated scope insertion section. Incidentally, the tether 27 of the magnet assembly has a minimal effect on the flexibility of the endoscope.

The subject is then intubulated with the endoscope, similar to the prior art technique shown in FIG. 1A. The surgeon advancing the distal end of the endoscope until the internal magnet is adjacent to an internal target location in the jejunum. The target location is confirmed using the optical features of the endoscope.

The surgeon then utilizes the illumination feature of the endoscope, By activating the light on the end of the endoscope, an external target area on the exterior surface of the abdominal wall is transilluminated. The external target area advantageously aligns with the internal target location.

The surgeon can now focus upon the method steps that utilize the magnet system of the present invention. An external magnet is used to magnetically couple with the internal magnetically couple with the internal magnet. FIGS. 4 and 5 show an internal magnet 25 coupled to an external magnet 40. As illustrated, the lumen 80, i.e., duct wall of a tubular organ, is stabilized against a portion of the abdominal wall 85 disposed at the internal target location. The improvement of the stabilizing of the lumen 80 advantageously permits ease of other method steps.

As illustrated, external magnet 40 includes a second coupling surface 45 defining a surface shape and size. The external magnet is characterized by a polar orientation and a magnetic strength. The polar orientation of the external magnet is opposite the polar orientation of the internal magnet such that the first and second coupling surfaces 28, 45 are magnetically attracted to each other. In order to increase magnet strength without increasing the surface area of the second coupling surface, a stack of external magnets may be used as illustrated in FIG. 7. In FIG. 7, a stack of magnets is illustrated within a protective disposable sleeve. In the practice of the invention, the stack may be an assembly of magnets, with the assembly having a fixed stack height. Alternatively, the stack may include removably joined magnets of equal diameter. Depending on several factors, e.g., the obesity of the subject, the stack may be increased or decreased in height, and consequently, magnetic strength.

As illustrated, the first coupling surface 28 and second coupling surface 45 have essentially the same shape and size. This allows for advantageous magnet aligning. The surgeon then prepares to insert a sounding needle into the subject at the external target area. The present invention allows for precise needle insertion at a desirable location. The surgeon determines a needle insertion point by observing a needle insertion zone. The external magnet includes structure defining a needle insertion zone. As illustrated in FIGS. 11a-11c, external magnets of various structure are disclosed. Various needle insertion zones 100, 101,102 are illustrated in the top views provided. Any suitable needle insertion point with in the zone may be chosen. Other alternative second coupling surface designs are illustrated in FIGS. 4, 5a and 5b.

In an alternative design of the present invention, only one of the internal magnet and external magnet are actually magnet, while the other one is merely iron.

A surgeon applies local anesthesia to the area around the needle insertion point and punctures the abdomen with a sounding needle 110. The sounding needle 10 is used to provide a small puncture into the lumen verify proper external location with respect to the desired internal location. By using the optical features of the endoscope, the surgeon then should verifying the sounding needle is properly positioned within the gastrointestinal tract. A properly inserted needle pierces only one wall & the lumen. Any suitable needle may be used in the practice of this invention. However, an advantageous needle size allows for a self heating wound when it is removed. The wound should clot well and present minimal risk of infection.

Once the surgeon verifies the sounding needle is properly located, a cannula 112 is inserted adjacent to the sounding needle. At this point, the sounding needle may be removed. The cannula has an inner center that is removed after insertion, leaving a hard plastic conduit that functions as a catheter. Others with ordinary skill in the art will appreciate other cannula designs may be used in the practice of this invention.

An exemplary sounding needle 110 and cannula 112 are illustrated in FIG. 1D.

A pull wire assembly 120 is then inserted through a passage formed within the cannula. The pull wire includes a mating end 122 and a pull end 124. The mating end is inserted into the cannula. The mating end 122 includes structure for providing a means to be grabbed by a snare. The mating end has no sharp edges or parts that may snag within the body. As illustrated, the structure is a loop, although other structure may be used in the practice & the present invention.

The surgeon now uses the snare assembly previously discussed. The snare assembly includes a snare 130, a snare operating device 132, and a cable 134 connecting the snare to the snare operating device. The snare is manipulated around the pull wire mating end. After the pull wire is secured by the snare, the internal magnet is decoupled from the external magnet by manually removing the external magnet from the abdominal wall. Gravity then acts upon the internal magnet causing it to fall away from the lumen.

The pull wire is pulled out of the gastrointestinal tract, up the esophagus, until the mating end is visible adjacent the subject's mouth. It is important that the pull end remained disposed outside the abdominal wall.

A feeding tube assembly is utilized by attaching a feeding tube assembly to the mating end. An exemplary feeding tube assembly 60 is illustrated in FIG. 6. The feeding tube assembly 60 includes a tube 62 having a first end 63 and a second end 64, a snare 65, a connector 67 fixedly joining the first end 63 to the snare 65, and a dome 68 fixed to the tube second end 64. The snare 65 is attached to the pull wire mating end. After attachment, the pull wire is used to install complete the installation of the feeding tube. By pulling of the pull end of the pulling tube, the dome is moved to within the intestines until, the dome abuts the gastrointestinal wall.

While a single embodiment of the invention has been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the annexed claims.

Having described my invention I claim:

1. A luminal coupling system for providing access directly to a lumen within a subject, for use with an endoscope having an instrument passage and an illumination source on a distal end, the system comprising:

a. an internal magnet assembly for inserting into an endoscope instrument channel, said internal magnet assembly comprising:
        i. an internal magnet comprising a first coupling surface defining a surface shape and size, wherein said internal magnet is characterized by a polar orientation and a magnetic strength; and
        ii. a tether comprising a first end portion fixed to said magnet, a second end portion disposed remote from said first end portion, and a middle portion spaced between said first and second end portions, said middle portion for traversing the endoscope instrument channel;
    b. a snare assembly comprising a first snare, a snare operating device, and a cable connecting said first snare to said snare operating device;
    c. an external magnet comprising a second coupling surface defining a surface shape and size, wherein said external magnet is characterized by a polar orientation and a magnetic strength, wherein said polar orientation of said external magnet is opposite said polar orientation of said internal magnet such that said first and said second coupling surfaces are magnetically attracted to each other;
    d. a pull wire system comprising a sounding needle, a cannula and a pull wire, wherein said pull wire comprises a mating end and a pull end; and e. a feeding tube assembly comprising a tube having a first end and a second end, a second snare, a connector fixedly joining said tube first end to said second snare, and a dome fixed to said tube second end.

2. The device claimed in claim 1 wherein said dome comprises a bottom surface having a tube mounting hole and an annular-shaped perforated side surface, said perforated side surface for distributing liquid in a plurality of radial directions.

3. The device claimed in claim 1 wherein said magnetic strength of said internal magnet and said magnetic strength of said external magnet are collectively sufficient to magnetically couple said internal and external magnets when juxtaposed of either side of an lumen wall.

4. The device claimed in claim 1 wherein said magnetic strength of said internal magnet and said magnetic strength of said external magnet are of collectively sufficient strength to stabilize an intestinal lumen to an abdominal wall when said magnets are juxtaposed of either side of an abdominal wall.

5. The device claimed in claim 1 wherein said surface shape and size of said first coupling surface and said surface shape and size of said second coupling surface are essentially the same.

6. The device claimed in claim 1 wherein said external magnet comprises structure defining a needle insertion zone.

7. The device claimed in claim 1 wherein said internal magnet comprises structure defining a needle acceptance zone.

8. The device claimed in claim 1 wherein said external magnet comprises structure defining a needle insertion zone, and said internal magnet comprises structure defining a needle acceptance zone, whereby said needle insertion zone and said needle acceptance zone cooperatively align when said external magnet and said internal magnet are magnetically coupled.

9. The device claimed in claim 1 wherein said internal magnet assembly comprises a lock for prohibiting said magnet from moving relative to a distal end of an endoscope when the internal magnet assembly is inserted into the instrument channel.

10. The device in claim 1 wherein said internal magnet comprises a coating of biocompatible material.

11. The device in claim 1 wherein said external magnet comprises a sleeve, said sleeve being disposable to protect the magnet during initial use and allow for subsequent use of said external magnet.

12. The device in claim 1 wherein said internal magnet is constructed of Neodymium Iron Boron (NdFeB).

13. The device in claim 1 wherein said external magnet is constructed of Neodymium Iron Boron (NdFeB).

14. The device in claim 1 wherein said external magnet comprises an assembly of similarly sized and shaped magnets, wherein a magnetic strength of said assembly can be varied by adding or deleting magnets to the assembly.

15. The device in claim 1 wherein a width of said external magnet is not greater than 1 inch.

16. The device in claim 1 wherein a width of said internal magnet is not greater than 1 inch.

* * * * *